(12) United States Patent
Wolff et al.

(10) Patent No.: US 6,577,887 B2
(45) Date of Patent: Jun. 10, 2003

(54) APPARATUS AND METHOD FOR IMPROVING DIAGNOSES

(76) Inventors: Floyd Wolff, PMB 416, 5030 Champion Blvd., Boca Raton, FL (US) 33496; Steven Wolff, 201 E. 69th St., Apt. #10-O, New York, NY (US) 10021

( * ) Notice: Subject to any disclaimer, the term of this patent is extended or adjusted under 35 U.S.C. 154(b) by 143 days.

(21) Appl. No.: 09/804,938

(22) Filed: Mar. 13, 2001

(65) Prior Publication Data

US 2002/0133071 A1 Sep. 19, 2002

(51) Int. Cl.⁷ ................................................. A61B 5/05
(52) U.S. Cl. .................... 600/411; 600/420; 600/422
(58) Field of Search ................................ 600/411, 420, 600/422

(56) References Cited

U.S. PATENT DOCUMENTS

| | | | |
|---|---|---|---|
| 5,400,787 A | * | 3/1995 | Marandos .................. 128/653.5 |
| 5,417,213 A | | 5/1995 | Prince |
| 5,435,303 A | | 7/1995 | Bernstein et al. |
| 5,543,710 A | * | 8/1996 | Jones .......................... 324/318 |
| 5,553,619 A | | 9/1996 | Prince |
| 5,592,086 A | | 1/1997 | Weinstock et al. |
| 5,706,813 A | * | 1/1998 | Filler et al. ................... 324/318 |
| 5,746,208 A | | 5/1998 | Prince |
| 5,762,065 A | | 6/1998 | Prince |
| 5,792,056 A | * | 8/1998 | Prince ........................... 600/420 |
| 5,924,987 A | | 7/1999 | Meaney et al. |
| 5,928,148 A | | 7/1999 | Wang et al. |
| 6,009,341 A | | 12/1999 | Edelman |
| 6,037,771 A | | 3/2000 | Liu et al. |
| 6,073,042 A | | 6/2000 | Simonetti |
| 6,137,291 A | * | 10/2000 | Szumowski et al. ......... 600/422 |
| 6,215,403 B1 | * | 4/2001 | Chan et al. .................. 600/481 |
| 6,375,620 B1 | * | 4/2002 | Oser et al. ................... 600/481 |
| 6,438,402 B1 | * | 8/2002 | Hashoian et al. ........... 600/410 |
| 6,445,945 B1 | * | 9/2002 | Arsenault .................... 600/431 |

\* cited by examiner

*Primary Examiner*—James Hook
(74) *Attorney, Agent, or Firm*—Robert R. Deleault, Esq.; Mesmer & Deleault, PLLC

(57) ABSTRACT

The apparatus and method alters the intravenous delivery of pharmaceuticals to enhance imaging of the vasculature of an animal. The apparatus includes a pressure-inducing component that is sized to attach circumferentially to an extremity of an animal thereby impeding arterial blood flow causing said pharmaceuticals to remain at selected levels within the vasculature.

27 Claims, 7 Drawing Sheets

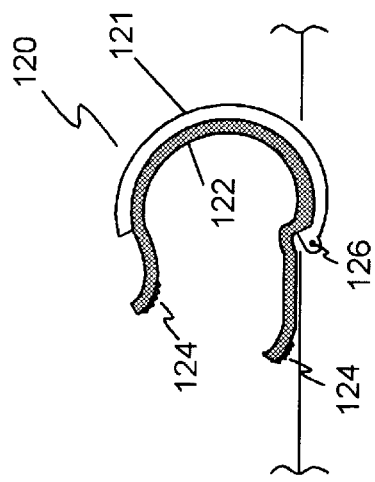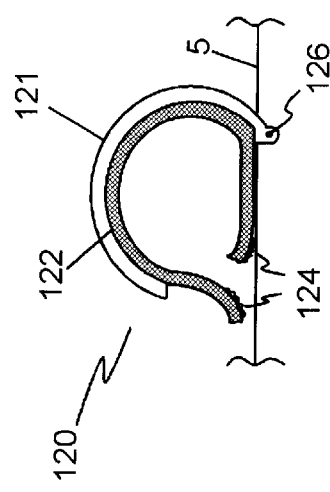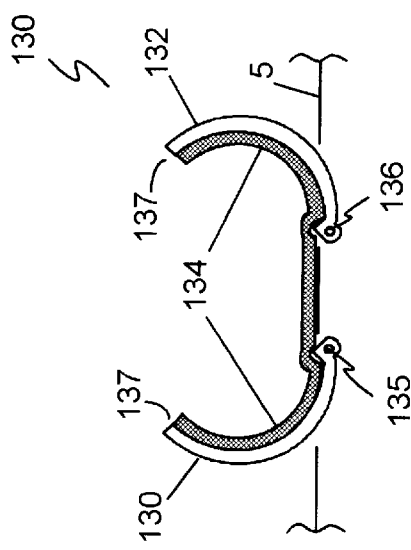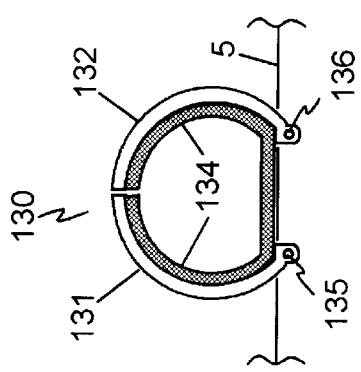

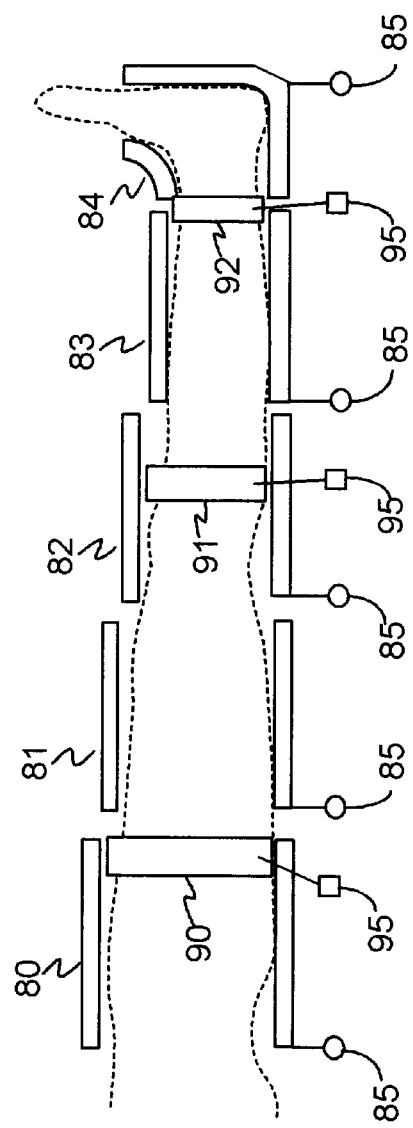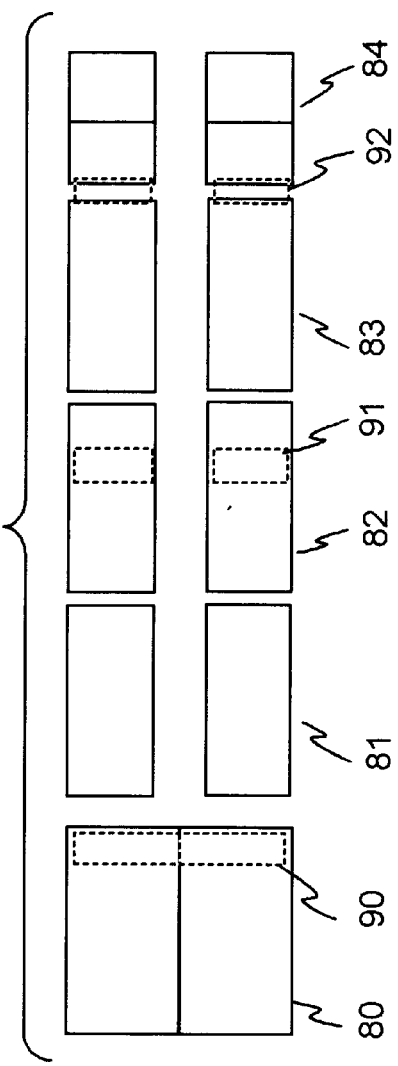

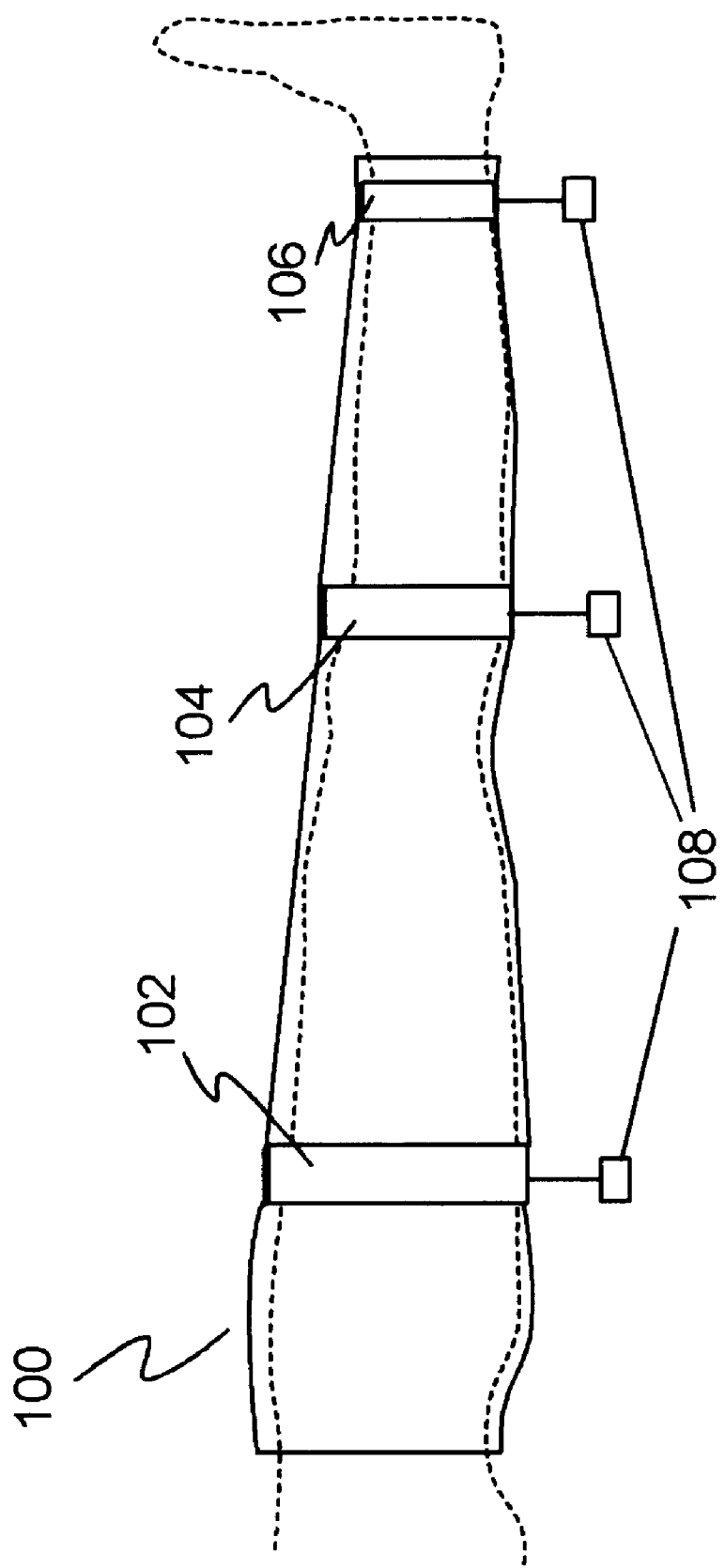

APPARATUS AND METHOD FOR IMPROVING DIAGNOSES

BACKGROUND OF THE INVENTION

1. Field of the Invention

The present invention relates generally to an apparatus and method for improving diagnoses. Particularly, the present invention relates to an apparatus and method for altering the intravenous delivery of pharmaceuticals to improve therapy and diagnosis. Even more particularly, the present invention relates to an apparatus and method for altering the intravenous delivery of pharmaceuticals to improve therapy and diagnosis using contrast agents that enhance nuclear magnetic resonance signals.

2. Description of the Related Art

Arterial diseases and injuries are common and sometimes have severe consequences including death. Imaging arteries serves to screen, detect and characterize arterial disease before these consequences occur. It also serves to define anatomic features that may provide assistance when planning surgery or vascular intervention.

In the practice of clinical medicine, numerous pharmaceutical products are administered intravenously. Some of these pharmaceuticals are used for diagnostic purposes and include contrast agents such as iodinated contrast-media used in x-ray angiography (XRA) and Computed Tomography Angiography (CTA), gadolinium chelates used in Magnetic Resonance Angiography (MRA) and radioactive agents used in nuclear medicine such as 99m-Tc-labeled Sestamibi or 201-Thallium. Some pharmaceuticals are administered intravenously for therapeutic purposes, for example, I-131 Sodium Iodide for thyroid cancer and perhaps in the future, pharmaceuticals for gene-therapy. All of these intravenously administered agents have in common the fact that they are distributed throughout the body by way of the blood stream.

One of the advantages of the x-ray techniques is that image data can be acquired at a high rate so that a sequence of images may be acquired during injection of the contrast agent. Such dynamic studies enable one to select the image in which the bolus of contrast agent is flowing through the vasculature of interest. Images showing circulation of blood in the arteries and veins of the kidneys, the neck and head, the extremities and other organs have immense diagnostic utility. Unfortunately, these x-ray methods subject the patient to potentially harmful ionization radiation and often require the use of an invasive catheter to inject a contrast agent into the vasculature to be imaged.

MRA uses the nuclear magnetic resonance (NMR) phenomenon to produce images of the human vasculature. When a substance such as human tissue is subjected to a uniform magnetic field, the individual magnetic moments of the spins in the tissue attempt to align with this polarizing field. A signal is emitted by the excited spins, and after the excitation signal is terminated, this signal may be received and processed to form an image. When utilizing these signals to produce images, magnetic field gradients are employed. Typically, the region to be imaged is scanned by a sequence of measurement cycles in which these gradients vary according to the particular localization method being used. The resulting set of received NMR signals are digitized and processed to reconstruct the image using one of many well-known reconstruction techniques.

To enhance the diagnostic capability of MRA, a contrast agent such as gadolinium can be injected into the patient prior to the MRA scan. Excellent diagnostic images may be acquired using contrast-enhanced MRA if the data acquisition is properly timed with the bolus passage. The non-invasiveness of MRA makes it a valuable screening tool for cardiovascular diseases. Screening typically requires imaging vessels in a large volume. This is particularly true for diseases in the runoff vessels of the lower extremity.

In MRA, contrast material injected into a vein in the upper extremity travels by vein to the right atrium of the heart. From there it travels to the right ventricle, then to the lungs where it is oxygenated. It returns to the left atrium of the heart, then to the left ventricle, the aorta, the common iliac artery, the internal and external iliac, the common femoral, and then throughout the smaller arteries of the thigh and leg. As the arterial blood passes through the lower extremities, it enters the capillaries of the muscles and then returns to the heart via the venous system. MRA of the lower extremities is done to visualize the vascular structures to determine the extent that some of the arteries (or veins) of the leg may be narrowed or partially blocked. Effective images can be made only while there is contrast material in the blood vessel being imaged. There exists only a short window of opportunity, approximately 30 to 45 seconds, when the contrast material is in the iliac, femoral and lower leg arteries when these images can be obtained and before the contrast material has entered the venous phase.

U.S. Pat. No. 5,928,148 (1999, Wang et al.) discloses a method of performing magnetic resonance angiography over a large field of view using table stepping. The MRA data is acquired from a large region of interest by translating the patient to successive stations at which successive portions of the MRA data set are acquired. Patient movement is chosen to track a bolus of contrast agent as it passes through the region of interest to achieve maximum image contrast. In one embodiment, a stationary local coil is supported adjacent the patient to acquire the MRA data. In another embodiment, a multi-segment local coil moves with the patient and its segments are sequentially switched into operation.

U.S. Pat. No. 5,924,987 (1999, Meaney et al.) discloses a method and apparatus for magnetic resonance arteriography using contrast agents. Meaney et al. disclose a technique of and a system for imaging vascular anatomy over a distance considerably greater than the maximum practical field of view of a magnetic resonance imaging system while using substantially one contrast agent injection. A plurality of image volumes are acquired that are representative of different portion's of the patient's body.

U.S. Pat. No. 5,553,619 (1996, Prince) discloses a method and apparatus for administration of contrast agents for use in magnetic resonance arteriography. The method and apparatus adapts the timing of a maximum or substantially elevated rate of infusion to correlate with the collection of image data corresponding to the center of k-space. Adapting the timing of a maximum or substantially elevated rate of infusion to correlate with the collection of image data corresponding to the center of k-space provides a period of a maximum or substantially elevated contrast concentration in the artery of interest relative to adjacent veins during collection of at least a portion of the image data corresponding to the center of k-space.

U.S. Pat. No. 5,417,213 (1995, Prince) discloses a method of imaging arteries distinctly from veins using nuclear magnetic resonance imaging in combination with intravenous administration of a magnetic resonance contrast agent. The contrast agent is injected in such a way that the arterial contrast concentration is substantially higher than the venous and background tissue concentration for a sufficiently long period of time to acquire the magnetic resonance image. The injection site of the contrast agent is chosen such that it is in a vein that is remote from the artery of interest.

U.S. Pat. No. 6,037,771 (2000, Liu et al.) discloses a sliding thin-slab method of acquiring three-dimensional MRA data. Liu et al. discloses the use of a 3DFT gradient-recalled echo pulse sequence to acquire NMR data from which an MR angiogram is produced. A thin slab excitation is employed and this thin slab is incremented in slice-thickness steps through the volume of interest as the NMR data is acquired. Navigator echoes are acquired at each thin slab location to correct the NMR data for phase errors produced by the sliding slab technique.

A disadvantage presented by the prior art is that the amount of imaging time required to make high-quality images is long compared to the amount of time the contrast material is in the arterial circulation. Effective images can be made only while there is contrast material in the blood vessel being imaged. The imaging time window is approximately 30 to 45 seconds after the contrast material enters the particular region to be imaged. Waiting too long before beginning the imaging shortens the already tight "window of opportunity" the technologist has to obtain the desired number of images. Imaging beyond the "window of opportunity" produces images of lesser and even poor quality with regard to the purpose for imaging the vasculature in the first place. This is so because the contrast material may have already passed through the arteries of the leg and into the veins. Imaging the veins provides the radiologist with no information about the state of the arteries, i.e. blockage of the arteries.

Another disadvantage of the prior art is directly related to the imaging "window of opportunity." Resolution in magnetic resonance imaging is a function of time. The longer the bolus of contrast material is in the arteries being imaged, the better the quality of the pictures.

Therefore, what is needed is an apparatus and method for extending the "window of opportunity" for imaging arteries containing a contrast agent. What is further needed is an apparatus and method for extending optimal imaging time by keeping the blood containing the contrast agent longer in the arteries undergoing imaging.

SUMMARY OF THE INVENTION

It is an object of the present invention to provide an apparatus and method for extending the imaging time when imaging arteries containing a contrast agent. It is another object of the present invention to provide an apparatus and method for extending optimal imaging time by keeping the blood containing the contrast agent longer in the arteries undergoing imaging. It is a further object of the present invention to provide an apparatus and method to regulate blood flow and, thus, affect the distribution of pharmaceuticals both proximal and distal to the site where the pressure is applied. It is yet another object of the present invention to provide an apparatus and method that alters the intravenous delivery of pharmaceuticals to improve therapy and diagnosis.

The present invention achieves these and other objectives by providing a device and method for raising the pressure in the veins of an extremity in order to slow the arterial blood flow. Imaging the lower extremities is done to visualize the arterial structures to determine the extent that some of the arteries of the leg may be narrowed and partially blocked. Effective images can be made only while there is contrast material in the blood vessel being imaged. Thus, there is only a short window of opportunity, approximately 30 to 45 seconds, when the contrast material is in the iliac, femoral and lower leg arteries to make the images. If an operator waits too long or does not have enough time to get the desired number of images, the blood containing the contrast material may have already passed through the arteries of the leg and into the veins.

Raising the pressure in the veins of an extremity in order to slow arterial blood flow allows the contrast agent to remain in the extremity longer providing higher resolution images. Because image resolution is a function of time, the longer the contrast material is in the arteries of the extremity, the better is the quality of the images that can be obtained. When the pressure applied to an extremity exceeds venous pressure, venous return of blood to the heart is slowed. When the pressure applied to an extremity exceeds diastolic pressure, arterial blood flow is slowed. When the applied pressure exceeds arterial systolic pressure, all blood flow is stopped. Varying degrees of pressure affect blood flow and thus affect the distribution and concentration of any intravenously administered chemical substance. The application of pressure to an extremity concomitant with the intravenous administration of a pharmaceutical can alter the amount of an agent that is delivered to that extremity. Furthermore, because altering the blood flow to an extremity can also alter the cardiac output, applying pressure to an extremity can modulate the delivery of an intravenous agent to other areas of the body as well.

The present invention applies pressure to one or more extremities to alter blood flow. For example, in imaging the lower extremities, external pressure is applied before, during, or after arrival of the pharmaceutical to the leg. If pressure is applied before the pharmaceutical arrives, the filling of the arteries with pharmaceutical is delayed and the transit time of the pharmaceutical is prolonged. The timing of the applied pressure relative to the circulation of the pharmaceutical may be optimized to image certain portions of the lower extremity vasculature (e.g. proximal arteries vs. distal arteries, arteries vs. veins, etc.). This technique may be used to enhance imaging of the vasculature using Magnetic Resonance Angiography (MRA), Computed Tomography Angiography (CTA), or X-ray Angiography (XRA).

By impeding arterial blood flow the present invention allows contrast material to remain visually active longer and at selected levels within the vasculature of the extremity. This achieves more signal and less noise thereby enhancing image resolution. The present invention uses one or more inflatable pressure cuffs to obtain better images during MRA (Magnetic Resonance Angiography) and CTA (Computed Tomography Angiography) by increasing the pressure in one or more extremities of the patient undergoing imaging. When inflated, the inflatable pressure cuffs affect blood flow and, thus, the concentration, duration of action and effectiveness of a contrast agent.

The present invention includes one or more inflatable cuffs connected to a cuff controller unit. The cuff controller unit is controlled and activated by a system controller. The system controller is programmed by an operator. Communication between the system controller and the cuff controller unit occurs by way of an interface. Interface coupling may be accomplished in any number of ways. Examples of such interface coupling are the use of cabling through the penetration panel, the use of electromagnetic control (e.g. infrared) through a window, or the use of optical fiber through a wave-guide.

The inflatable cuffs may be incorporated into an extremity peripheral vascular radio frequency (rf) coil array. The rf coil array and cuffs may be components of a structured table system. The cuffs may be further incorporated into an extremity holding system coupled to the table system. The extremity holding system may be a pivoting, arcuate component that is positioned around the extremity. The arcuate component may be multiple pieces with each piece adapted to incorporate a cuff, or the arcuate component may be a single, extremity-long device having a plurality of predetermined locations adapted to incorporate a cuff in each predetermined location. The pivoting arcuate component of the extremity holding system may also be a two-piece, jaw-like component where each jaw-like component is adapted to pivot towards its other mating component into a closed position to encircle a portion of the extremity and to pivot away from each other into an open position to allow placement or removal of an extremity. The rf coil array and cuffs may also be configured together into a stocking-like or pant-like garment structure that clothes the patient's extremity undergoing the imaging. The rf coils may be paired to provide upper and lower halves of the rf coils. Alternate geometries of rf coils are also possible such as a series of volumetric coils with each element including both extremities.

For use with existing MRA systems, a pressure-cuff system is employed that includes one or more pressure-inducing bands or cuffs and a pressure-inducing controller unit. The one or more pressure-inducing bands or cuffs may be individually placed about the extremity of an animal, and more particularly a human being, or they may be incorporated into a stocking-like or pant-like garment made of a flexible material. Preferably the garment has a releasable seam that allows the extremity to be easily enclosed/encircled by wrapping the garment structure about the extremity. Each one or more pressure-inducing bands or cuffs is coupled to the controller unit, which in turn is controlled by an operator or by a computer program or both. Each pressure-inducing band or cuff is individually controlled to provide the required pressure in the extremity for enhancing the MRA images.

BRIEF DESCRIPTION OF THE DRAWINGS

FIGS. 5A and 5B are cross-sectional views of one embodiment of the pressure-inducing cuff of the present invention showing the closed and open position of a pivoting cuff affixed to a patient table.

FIGS. 6A and 6B are cross-sectional views of another embodiment of the pressure-inducing cuff of the present invention showing the closed and open position of a two-piece pivoting cuff affixed to a patient table.

FIG. 7A is a side view illustration of the present invention configured in a stocking-like structure showing the upper and lower halves of the rf coils and the inflatable cuffs around a lower extremity.

FIG. 7B is a top view illustration of the present invention shown in FIG. 7A showing the upper rf coil array and the inflatable cuffs.

FIG. 8 is a side view illustration of another embodiment of the present invention showing a garment structure that incorporates a plurality of pressure-inducing bands or cuffs.

DETAILED DESCRIPTION OF THE PREFERRED EMBODIMENT

Figure 1:
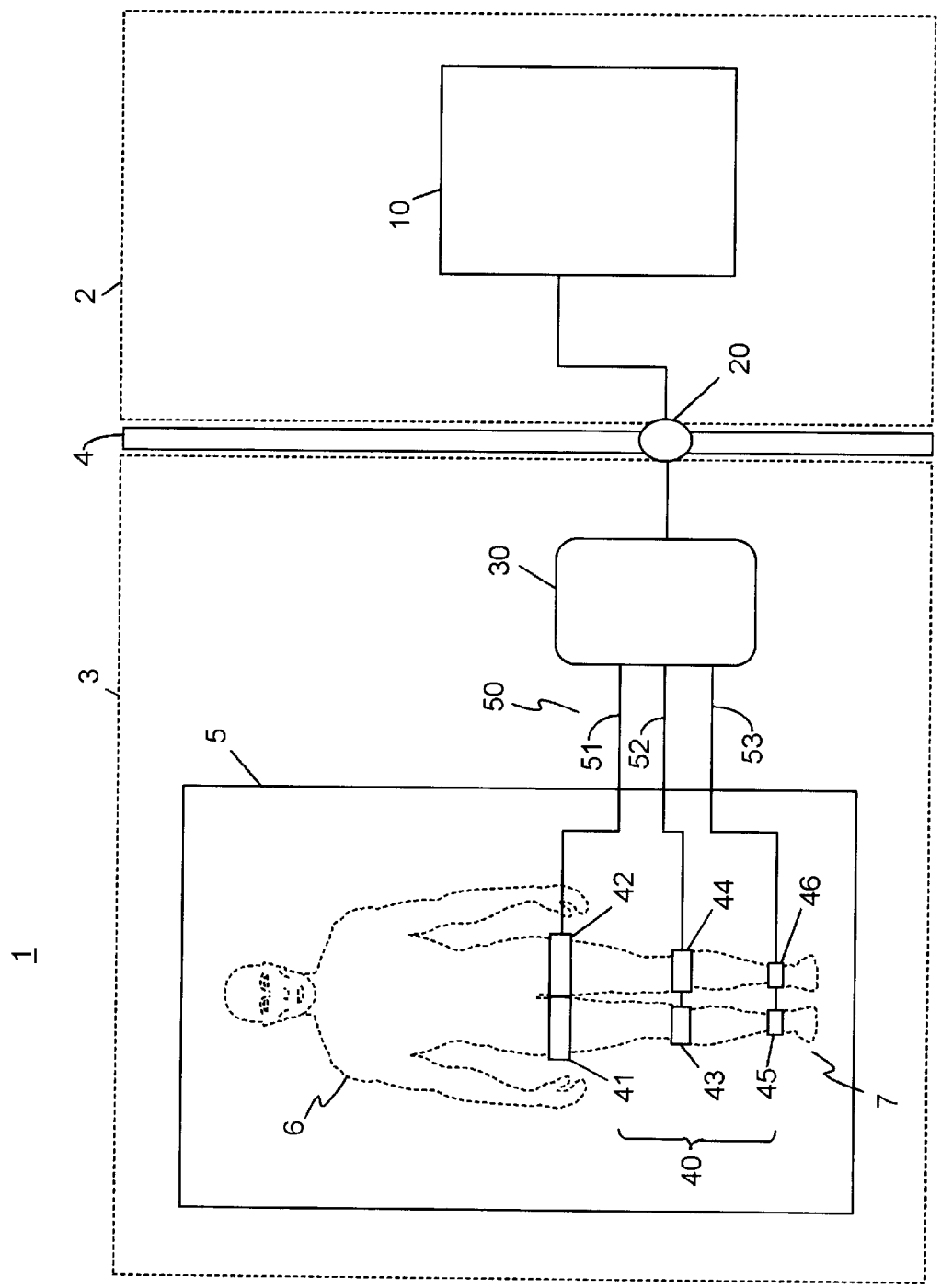
FIG. 1 is a schematic illustration showing the various components used with the present invention.

The preferred embodiment of the present invention is illustrated in FIGS. 1–8. FIG. 1 shows an imaging system 1 having a control room 2, a scan room 3 and a penetration panel 4 situated between control room 2 and scan room 3. Scan room 3 includes scan table 5 upon which is placed a patient 6 undergoing imaging. In this case, a set of inflatable cuffs 40 is placed around the lower extremities 7 of patient 6. Inflatable cuffs 40 include a right upper cuff 41, a left upper cuff 42, a right middle cuff 43, a left middle cuff 44, a right lower cuff 45, and a left lower cuff 46. The inflatable cuffs 40 may be wide like a blood pressure cuff or narrow like a tourniquet band. Although inflatable cuffs are preferred, it will be understood by those skilled in the art that any cuff or band capable of tightening around an extremity to impede blood flow through the extremity can be used. For instance, the cuff or band may be made out of a resilient and stretchable material such as rubber.

Inflatable cuffs 40 are connected to a cuff controller unit 30 by way of a control line system 50. Control line system 50 includes a first control line 51 for controlling right upper cuff 41 and left upper cuff 42, a second control line 52 for controlling right middle cuff 43 and left middle cuff 44, and a third control line 53 for controlling right lower cuff 45 and left lower cuff 46. Each of the control lines 51, 52 and 53 incorporates separate control lines for the right and left cuff thereby allowing each cuff to be activated and controlled independently, if desired. Cuff controller unit 30 inflates and deflates inflatable cuffs 40 at predetermined times relative to the injection of intravenous contrast agent, depending on the imaging detail wanted. The amount of inflation pressure required to impair blood flow in the arteries of the lower extremity to enhance imaging may vary. For instance, raising pressure above the venous pressure by just a few millimeters of mercury may be sufficient to achieve the desired effect. In other cases, it might be necessary to totally occlude the arterial blood flow, in which case it would be necessary to raise the pressure just above the arterial systolic blood pressure, i.e. approximately 110 mm to approximately 200 mm Hg.

A fluid material such as gases or liquids may be used to operate inflatable cuffs 40. Examples of usable gases are air, compressed air, helium, nitrogen, carbon dioxide, and the like. Examples of usable liquids are water, oil and the like. Preferably, a compressor is used to inflate inflatable cuffs 40 using compressed air.

Control room 2 includes the system controller 10 that controls the operation of imaging system 1. System controller 10, which is programmed by an operator, controls and activates cuff controller unit 30. Coupling of system controller 10 to cuff controller unit 30 is accomplished though an interface coupler 20. Interface coupler 20 may couple system controller 10 to cuff controller unit 30 in any number of ways. Examples of such interface coupling are the use of cabling through penetration panel 4, the use of electromagnetic control (e.g. infrared) through a window (not shown), or the use of optical fiber through a wave-guide.

Figure 2:
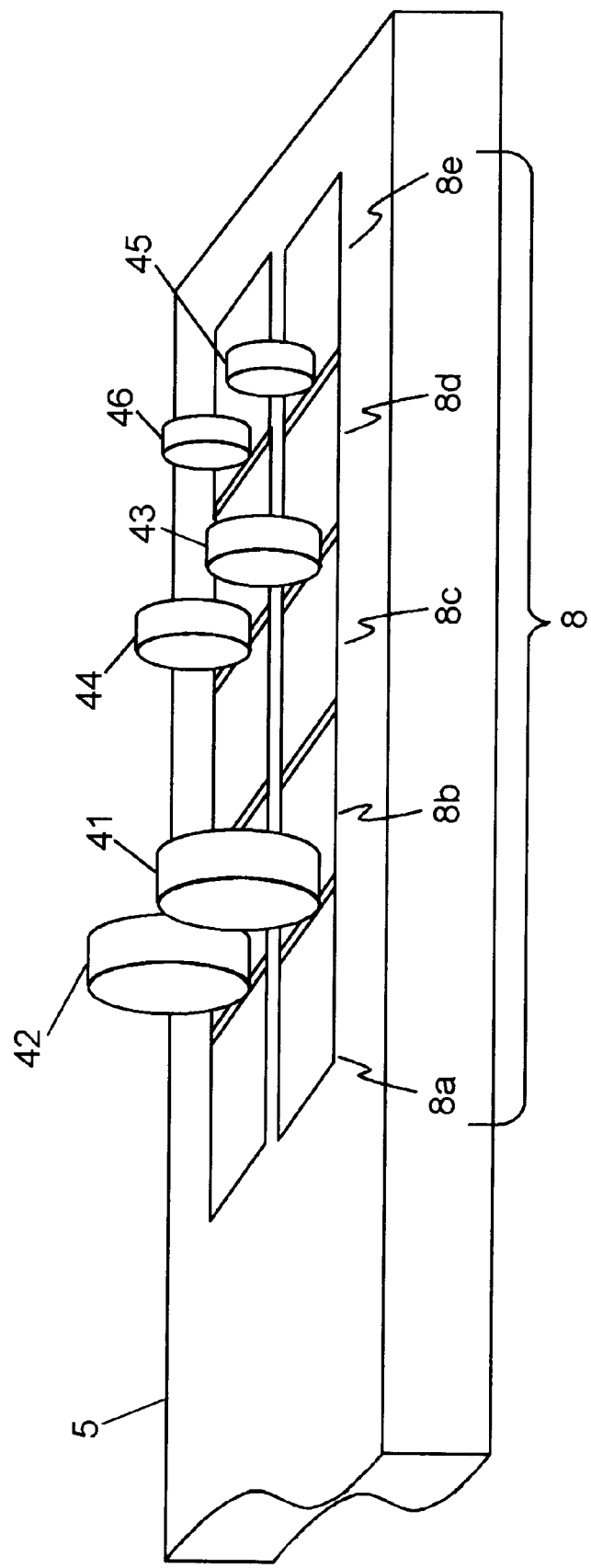
FIG. 2 is a perspective view illustration showing an inflatable cuff system of the present invention into a lower extremity peripheral vascular array.

Turning now to FIG. 2, inflatable cuff system 40 is shown incorporated into a lower extremity peripheral vascular rf coil array. Because an entire lower extremity is too long to be imaged in its entirety at one instant by an imaging system, the scanner and table area must be moved and be able to follow the contrast material as it flows from thigh to lower leg to foot. The system may have a single coil or multiple coil arrays for imaging the entire lower extremity.

Figure 3:
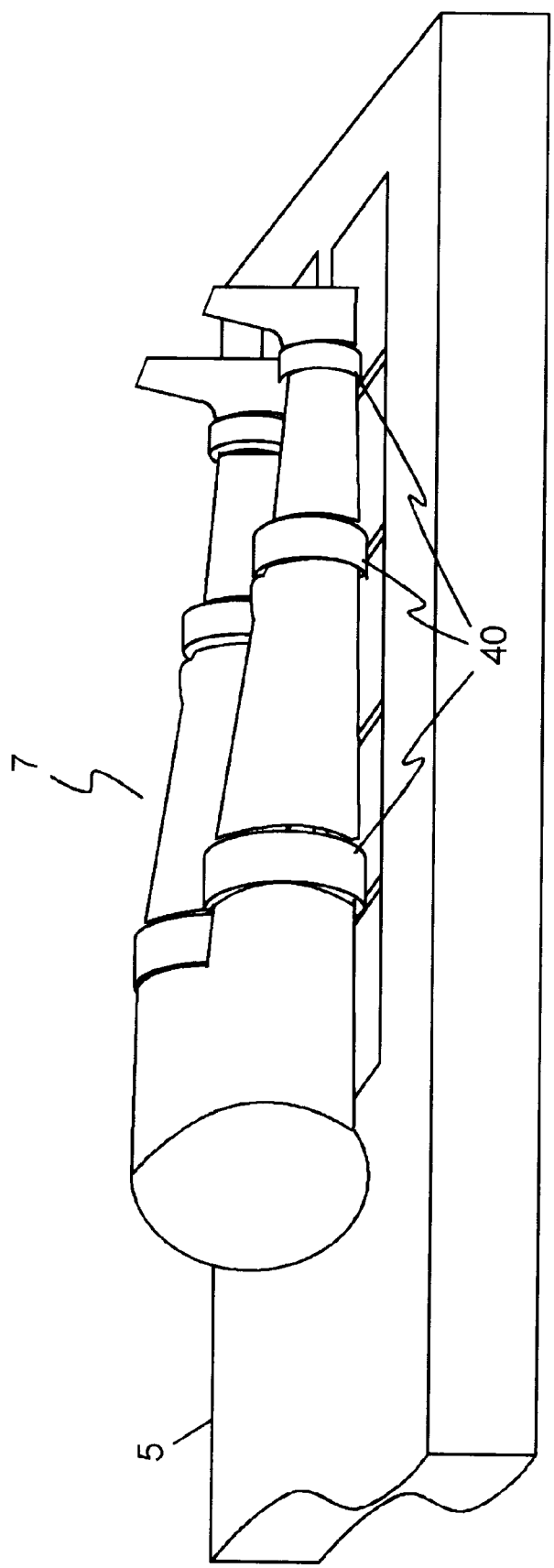
FIG. 3 is a perspective view illustration of the present invention showing the relationship among the lower array of rf coils, the inflatable cuffs and the lower extremities.
Figure 4:
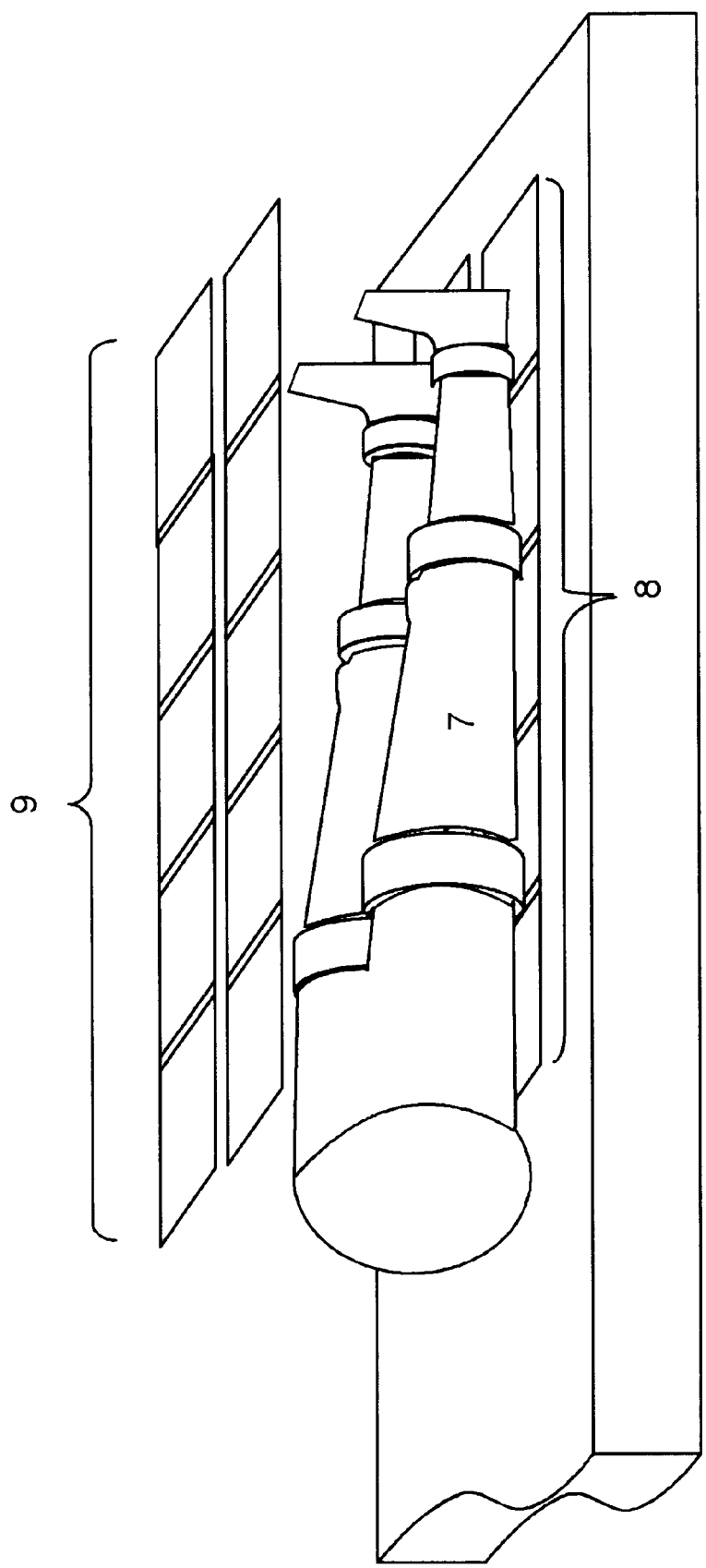
FIG. 4 is a perspective view illustration of the present invention showing the relationship among the inflatable cuffs, the upper and lower halves of the rf coils and the lower extremities.

In the present invention, patient table 5 includes inflatable cuffs 41, 42, 43, 44, 45, and 46 as well as the five pairs of rf coils 8a, 8b, 8c, 8d, and 8e that comprise the lower half of the phased-array rf coils 8. The lower rf coils 8 are paired to image the right and left extremity simultaneously, if desired. Each pair of rf coils is activated when the contrast agent is within the segment of the extremity that is within the field of view of that particular pair. Generally, only one pair of rf coils is activated at a time. Each inflatable cuff can be activated independent of the other cuffs. FIG. 3 shows placement of the lower extremities 7 within inflatable cuffs 40. FIG. 4 shows the relationship among the inflatable cuffs 40, the lower extremities 7, and the upper and lower halves of rf coils 8 and 9.

The inflatable cuffs may also be entirely separate and secured to the lower extremity by simple wrapping. Alternatively, the inflatable cuffs can be incorporated into the patient table by way of pivoting bands or leg enclosures. FIGS. 5A and 5B illustrate one embodiment of such a pivoting band enclosure. FIGS. 5A (closed position) and 5B (open position) show a pivoting band enclosure system 120 having an outer rigid frame 121 that has an arcuate shape with a pivot 126 affixed to patient table 5. Within the outer rigid frame 121 is situated an inflatable cuff 122. Patient table 5 may include one or more of pivoting band enclosure system 120. Inflatable cuff 122 has mating fasteners 124 that allow inflatable cuff 122 to fasten upon itself and completely encircle the extremity. Preferably, the mating fasteners 124 are hook and loop type fasteners. Where a leg enclosure embodiment is used, patient table 5 would include a pivoting leg enclosure for each extremity and each enclosure would include one or more of inflatable cuff 122 positioned along the inside of the leg enclosure at appropriate and predetermined locations.

An alternative embodiment of the band or leg enclosure system shown in FIGS. 5A and 5B is the band or leg enclosure system shown in FIGS. 6A and 6B. The band enclosure system 130 includes a first cuff frame 131 connected to patient table 5 by first frame pivot 135, a second cuff frame 132 connected to patient table 5 by second frame pivot 136, and an inflatable cuff 134. Inflatable cuff 134 is coupled to first cuff frame 131 and second cuff frame 132 so that ends 137 of band enclosure system 130 are in an opposed relationship when first and second cuff frames 131 and 132 swing from an open position as shown in FIG. 6B to a closed position as shown in FIG. 6A thereby encircling the patient's extremity when in use. Where a full-length extremity enclosure system is used having a similar first and second cuff frame structure, one or more inflatable cuffs are situated at predetermined locations along the extremity cuff frame of the extremity enclosure system.

An alternative local coil and cuff structure that moves with the patient may also be used. Referring now to FIGS. 7A and 7B, this alternative local coil and cuff is a coil array comprised of five coil segments 80–84, each comprised of four coil elements. Coil segments 80–84 are positioned on the patient and distributed along the entire region of interest to be imaged. In this case, it is the legs and the feet. Also incorporated is an inflatable cuff array comprised of three cuff components 90–92, each comprised of two cuff elements, one for each extremity. Cuff components 90–92 are positioned along the extremity to provide pressure before, during or after the infusion of an intravenous contrast agent. The coils and cuffs are supported by fabric (not shown) that is sewn into a stocking-like or pant-like garment that clothes one or more of the patient's legs.

Each coil segment 80–84 has four coil elements that acquire NMR data from the field of view. Two of the coil elements are positioned on top, or anterior, of the lower extremity as seen in FIG. 7B, and the other two elements are positioned below, or posterior, of the lower extremity. The coil elements connect together to form one of the coil segments 80–84 and each is separately connected through terminals 85 to the imaging system 1.

Each cuff component 90–92 has two cuff elements that are capable of obstructing blood flow to a portion of each extremity. One of the cuff elements is positioned around one extremity and the other cuff element is positioned around the other extremity. Each cuff element is connected to the compressor by way of terminals 95 and each can be individually controlled, or can be controlled simultaneously, to obstruct blood flow to a portion of the extremity before, during or after introduction of the intravenous contrast agent.

Another embodiment of the present invention for use with existing imaging machines is illustrated in FIG. 8. This particular embodiment incorporates one or more compression bands or cuffs 102, 104 and 106 in a stocking-like or pant-like structure 100 that extends from the foot to either the inguinal or waist area. The stocking-like or pant-like garment is worn by the patient and each compression band or cuff 102, 104 and 106 is connected by way of couplers 108 to the cuff controlling unit. In the stocking-like embodiment, the stocking may be slipped on over the extremity like a tube of fabric, or the garment may have a releasable seam along its length, or the garment may be more like a wrap that wraps around the extremity much like a blood-pressure cuff wraps around the upper arm. The releasable seam allows the extremity to be enclosed without sliding the stocking-like or pant-like garment over the entire length of the extremity. The releasable seam may be fastened using a zipper, a plurality of snaps or buttons, or hook and loop fasteners placed along the length of the seam or strategically placed to coincide with the inflatable cuffs like that used for blood pressure cuffs.

As described earlier, the timing for activating one or more of the pressure cuffs in any of the embodiments depends on the image optimization required, i.e. the pressure is optimized to image certain portions of the lower extremity vasculature such as proximal arteries versus distal arteries, arteries versus veins, etc.

Although the preferred embodiments of the present invention have been described herein, the above description is merely illustrative. Further modification of the invention herein disclosed will occur to those skilled in the respective arts and all such modifications are deemed to be within the scope of the present invention as defined by the appended claims.

What is claimed is:

1. A vasculature image enhancing apparatus comprising:
  one or more flexible pressure-inducing components sized to fit around an animal extremity wherein each of said one or more flexible components is positioned before the area in said animal extremity to be imaged and wherein said pressure-inducing component is engaged at a predetermined time before, during or after intravenously delivering a predetermined amount of an intravenous material in said animal thereby affecting blood flow and affecting the concentration, amount or duration of action of said intravenous material in said extremity thereby enhancing imaging of the vasculature of an animal.

2. The apparatus of claim 1 wherein said pressure-inducing component includes one or more pressure-inducing bands.

3. The apparatus of claim 1 wherein said pressure-inducing component is one or more inflatable cuffs.

4. The apparatus of claim 1 wherein said pressure-inducing component is a tourniquet.

5. The apparatus of claim 1 wherein said apparatus incorporates at least one coil for reception of data to form a nuclear resonance image.

6. The apparatus of claim 1 wherein said pressure-inducing component is adapted to be selectively engaged for applying intermittent pressure to an animal's extremity.

7. The apparatus of claim 1 wherein said one or more pressure-inducing components is encased in a stocking-like structure adapted to fit over an extremity of said animal.

8. The apparatus of claim 7 wherein said stocking like structure further includes said at least one coil.

9. A method for altering the intravenous delivery of materials in an animal to enhance vasculature imaging, said method comprising:

attaching to an animal extremity at least one pressure-creating device for raising the pressure in said animal extremity wherein said at least one pressure-creating device is positioned before the area in said animal extremity to be imaged;

delivering intravenously a predetermined amount of an intravenous material in said animal; and activating at a predetermined time said at least one device sufficient to raise the pressure in said animal extremity to slow the flow of blood in said extremity for a predetermined period of time.

10. The method of claim 9 further comprising engaging said at least one device before said intravenous material enters said extremity thereby delaying the filling of blood vessels of said extremity with said intravenous material.

11. The method of claim 9 further comprising engaging said at least one device before said intravenous material enters said extremity thereby altering cardiac output in order to alter the concentration and transit time of intravenous material in the arterial circulation.

12. The method of claim 9 further comprising engaging said at least one device at a predetermined time before, during or after arrival of said intravenous material in said extremity to image preselected portions of the vasculature of said extremity.

13. The method of claim 9 further comprising engaging said at least one device at a predetermined time after said intravenous material enters said extremity thereby allowing said intravenous material to remain within said extremity for a longer period of time.

14. The method of claim 9 further comprising engaging said at least one device at a predetermined time while said intravenous material is entering said extremity.

15. The method of claim 9 further comprising engaging said at least one device at a predetermined time sufficient to interrupt the blood flow to said extremity and then disengaging said at least one device to restore the blood flow thereby achieving a transitory augmentation of arterial perfusion of said intravenous material.

16. The method of claim 9 further comprising engaging said at least one device at a predetermined time sufficient to interrupt the blood flow to said extremity and then disengaging said at least one device to restore the blood flow thereby altering cardiac output in order to alter the concentration and transit time of intravenous material in the arterial circulation.

17. The method of claim 9 further comprising engaging said at least one device to a pressure great enough to stop both arterial and venous blood flow.

18. The method of claim 9 further comprising engaging said at least one device to a pressure great enough to stop venous blood flow without stopping arterial blood flow.

19. The method of claim 9 further comprising engaging said at least one device to a pressure great enough to slow venous blood flow without stopping arterial blood flow.

20. An apparatus for enhancing images of the vasculature obtained using an intravenous contrast agent, said apparatus comprising:

a plurality of inflatable cuffs adapted to be situated around an animal extremity at predetermined locations wherein said predetermined locations are located before the area in said animal extremity to be imaged; and a cuff controller unit adapted to activate each of said plurality of inflatable cuffs at predetermined times.

21. The apparatus of claim 20 further comprising an extremity enclosing structure that incorporates said plurality of inflatable cuffs.

22. The apparatus of claim 21 wherein said extremity enclosing structure is a stocking-like or pant-like structure.

23. The apparatus of claim 20 further comprising a system controller unit adapted to control said cuff controller unit.

24. The apparatus of claim 23 wherein said system controller unit communicates with said cuff controller unit through wires connected to a scan room penetration panel.

25. The apparatus of claim 23 wherein said system controller unit communicates with said cuff controller unit using electromagnetic radiation transmitted through a scan room window.

26. The apparatus of claim 23 wherein said system controller unit communicates with said cuff controller unit through optical fiber passing into a scan room by way of a waveguide.

27. An apparatus for enhancing imaging of the vasculature of an animal, said apparatus comprising:

an imaging device for imaging an animal wherein said imaging device has at least one coil and wherein said imaging device provides images using nuclear resonance imaging technology; and a flexible pressure-inducing component sized to fit around an animal extremity wherein said flexible pressure-inducing component is positioned before the area in said animal extremity to be imaged and wherein said pressure-inducing component is engaged at a predetermined time before, during or after intravenously delivering a predetermined amount of an intravenous material in said animal thereby affecting blood flow and affecting the concentration, amount or duration of action of said intravenous material in said extremity.

* * * * *